United States Patent [19]

Angres

[11] Patent Number: 5,179,097

[45] Date of Patent: Jan. 12, 1993

[54] SALTS OF NON-STEROIDAL ANTI-INFLAMMATORY CARBOXYLIC ACIDS AND ANTI-LIPIDEMIC CARBOXYLIC ACIDS

[76] Inventor: Isaac A. Angres, 6 War Admiral Ct., Gaithersburg, Md. 20878

[21] Appl. No.: 712,536

[22] Filed: Jun. 10, 1991

[51] Int. Cl.$^5$ .................. A61K 31/24; A61K 31/215; A61K 31/235; A61K 31/495

[52] U.S. Cl. .................. 514/255; 514/356; 514/473; 514/531; 514/533; 514/534; 514/539; 514/568; 514/570; 514/571; 514/653; 514/824; 544/406; 546/318; 560/36; 560/39; 560/61; 560/62; 560/110; 560/52; 560/205

[58] Field of Search .................. 546/318; 544/406; 562/421, 468, 598; 560/61, 36, 39, 62, 110, 205, 52; 514/255, 473, 356, 824, 568, 653, 571, 570, 539, 531, 533, 534

[56] References Cited

U.S. PATENT DOCUMENTS

| | | | |
|---|---|---|---|
| 3,716,583 | 2/1973 | Nakamura et al. | 514/824 |
| 4,002,750 | 1/1977 | Ambrogi et al. | 544/406 |
| 4,244,958 | 1/1981 | Jirkovsky et al. | 549/479 |
| 4,552,899 | 11/1985 | Sunshine et al. | 514/653 |

OTHER PUBLICATIONS

Merck Index, 9th Edition, 106, A1, 6337, 5184, 2375, 4280, 2353, 1215, 2314, 9980, 8976, 3495, 6895, 6435, 4812.

*Primary Examiner*—Cecilia Tsang
*Attorney, Agent, or Firm*—Isaac Angres

[57] ABSTRACT

Novel choline salts of non-steroidal anti-inflammatory carboxylic acids and anti-lipidemic carboxylic acids are described. Additionally, blends of choline salts with the above carboxylic acids are also described. The new salts and compositions offer new therapeutic advantages.

20 Claims, No Drawings

SALTS OF NON-STEROIDAL ANTI-INFLAMMATORY CARBOXYLIC ACIDS AND ANTI-LIPIDEMIC CARBOXYLIC ACIDS

The present invention relates to novel choline salts of non-steroidal anti-inflammatory carboxylic acids and anti-lipidemic carboxylic acids. The salts are made by reacting choline chloride with the sodium salt of the aforementioned carboxylic acids.

DESCRIPTION OF THE PRIOR ART

Non-steroidal anti-inflammatory carboxylic acids such as those of the salicylic, acetic, propionic, byphenyl, and diphenyl ether series are well known both in the market place and the patent literature. Typical acids include ibuprofen, naproxen, aspirin, as well as all those listed in U.S. Pat. No. 4,552,899 whose contents are incorporated by reference herein.

Numerous anti-lipidemic carboxylic acids have been discovered, patented, as well as marketed. Among the most prominent anti-lipidemic carboxylic acids are: 2,2-dimethyl-5-(2,5-xylyloxy) valeric acid (gemfibrozil) described in U.S. Pat. Nos. 3,674,836 and 4,126,637; α-(p-chlorophenoxy) isobutyric acid (clofibric acid) described in British Patent No. 860,303; 2,2'-(4, 4'- cyclohexylidene diphenoxy)- 2,2'-dimethyl butyric acid (clinofibrate) described in U.S. Pat. No. 3,716,583, - [4-(4-chlorobenzoylaminethyl) phenoxy] isobutyric acid (Bezafibrate) disclosed in U.S. Pat. No. 3,781,328, 2-[4-(2,2-dichlorocyclopropyl) phenoxy] isobutyric acid (ciprofibrate) taught in U.S. Pat. No. 3,948,973; (4-biphenylyl) butyric acid (xenbucin) disclosed in British Patent No. 1,168,542; 5-methyl pyrazine carboxylic acid -4-oxide (acipimox) described in U.S. Pat. No. 4,002,750; 3-pyridine carboxylic acid 1-oxide featured in Belgian Patent No. 618,968; 4,5-dihyro-5-methyl-4-oxo-5-phenyl-2-furam carboxylic acid 5-methyl-4-oxo-5-phenyl -2-furam carboxylic acid (Acifram) described in U.S. Pat. Nos. 4,169,202 and 4,244,958; 5, 8, 11, 14, 17, -Eicosapentaenoic acid; and sultosilic acid disclosed in U.S. Pat. No. 3,954,767.

Certain choline salts such as choline salicylate and choline dihydrogen tartrate are disclosed in U.S. Patent Nos. 3,069,321 and 2,870,198 respectively.

Choline is (β-hydroxyethyl) trimethylammonium hydroxide. Since it is completely dissociated, it is

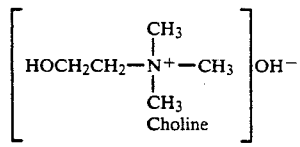

comparable to alkali hydroxides as a base. Consequently, it does not exist as a base at body pH but rather as a salt, the anion is that present in its immediate biological environment. The β-(hydroxyethyl) trimethylammonium cation is the biologically important moiety. The cation is incorporated into phospholipids, such as licithin and sphingomyelin, and acetylcholine, a substance released at cholinergic nerve junctions during transmission of nerve impulses. Acid hydrolysis of phopholipids yields the free choline salt which is very soluble in water, and to a lesser extent in ethanol.

Besides its vital function as a precursor of acetylcholine, which is important in the sequence of nerve muscle stimulations, choline is an important contributor of metabolites and perhaps some hormones. The biogenesis of choline appears to be universal in nature, and is the result of the three-step transfer of methyl groups to an acceptor, which may be either free aminoethanol or phosphatidyl aminoethanol. Such transfers require methionine as a methyl donor (actually, S-adenosylmethionine). Choline is indirectly a source of methyl groups: it is first oxidized to betaine, which then may transfer a methyl group to homocysteine to form methionine. By thus regenerating methionine lost in transmethylation reactions, exogenous choline can spare the amino acid for use in protein synthesis. Methionine is an essential amino acid.

Choline has the property of preventing the deposition of excess fat, or of causing the removal of excess fat from the liver of experimental animals fed high-fat diet and, because of this, is often classified as a "lipotropic agent". The lipotropic action probably relates to the incorporation of choline into phosphatidyl choline (lecithin), which, in turn, is incorporated into phospholipids and liproteins. The lipotropic action is independent of the function of choline as a resevoir of methyl groups.

Addtionally, it is well known that any NSAD's such as the ones having carboxylic acid functions can upset the stomach of many patients. Similar effects have been observed with the anti-lipidemic carboxylic acids.

It has long been recognized that certain conditions or diseases, such as coronary heart disease and atherosclerosis, are associated with and may be caused by the presence of too high a level of cholesterol in the blood plasma; and for the treatment of such condition many attempts have been made to find means for reducing the cholesterol level in blood plasma, for instance by provision of some kind of orally-administerable pharmaceutical preparation capable of exerting a hypocholesterolaemic effect, that is to say reducing the cholesterol level in blood plasma and thus combating hypercholesterolaemia.

It has now been found that, from amongst the wide variety of preparations, both in the nature of drugs and other products, which have hitherto been employed for the reduction of blood-cholesterol levels, it is possible to select combinations which exhibit a quite unexpectedly enhanced or synergistic effect, as will be described hereinafter. The selected combinations which display this peculiar and valuable therapeutic property are formed between certain known synthetic blood cholesterol-reducing drugs and certain choline compounds. Although may be known that some of the latter can also reduce blood cholesterol, what is surprising is that when used in combination they can quickly achieve, in at least a large proportion of patients suffering from hypercholesterolaemia, a reduction in blood cholesterol which is greater than can be hoped for with one of the synthetic blood cholesterol-reducing drugs alone and also faster that could be expected with one of the choline compounds alone, or even both of them jointly. The use of this synergistic combination of blood cholesterol-reducing agents thus opens the way to significant improvements in the treatment of hypercholesterolaemia.

The combination needed to attain these remarkable results is formed either by making the choline salts of the anti-lipidemic carboxylic acids or by blending the anti-lipidemic carboxylic acid with a choline salt, i.e., choline citrate or choline dihydrogen tartrate.

3

The problem of upset stomachs by NSAD's is also addressed by blending the non-steriodal anti-inflammatory carboxylic acid with a choline salt or by making the salt as discussed above in connection with the anti-lipidemic carboxylic acids.

SUMMARY OF THE INVENTION

The primary object of the present invention is to provide the choline salts of non-steroidal anti-inflammatory carboxylic acid.

Another object of the present invention is to provide the choline salts of anti-lipidemic carboxylic acids.

An additional object of the present invention is to provide compositions of matter comprising non-steroidal carboxylic acids and choline salts.

Still another object of the present invention is to provide compositions of matter comprising anti-lipidemic carboxylic acids and choline salts.

A further object of the present invention is a method for enhancing the anti-lipidemic effect of anti-lipidemic carboxylic acids by administering concurrently a choline salt.

DESCRIPTION OF THE PREFERRED EMBODIMENTS

The present invention deals with components having the following formula:

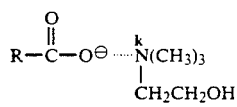

wherein R represents a chemical moiety selected from the group comprising non-steriodal anti-inflammatory carboxylic acids excluding the salicylates and anti-lipidemic carboxylic acids.

The compounds of the present invention are prepared by reacting the sodium salt of the carboxylic acid with choline chloride in a suitable solvent such as acetone or isopropyl alcohol. After reaction the precipitated sodium chloride is filtered and then the resulting choline salt is obtained by evaporating the solvent.

The preferred non-steroidal carboxylic acids include the arylacetic acids, the fenamic acids, the aryl propionic acids and the biphenyl carboxylic acids.

Typical acids include ibuprofen, diflunisal, fenoprofenic acid, meclofenic acid, mefenamic, acid, naproxen, sulindac, indomethacin, talmetin, fenbufen, ketoprofen, indoprofen, fluprofen, benozaprofen, pirprofen, miroprofen, and thioxaprofen.

The preferred anti-lipidemic carboxylic acids are clofibric acid, gemfibrozil, clinofibrate, bezafibrate, ciprofibrate, xenbucin, acipimox, acifram, sultosilic acid, eicosapentaenoic acid, oxiniacic acid, and nicotinic acid.

In another emobodiment of the present invention, the non-steriodal carboxylic acids and anti-lipidemic carboxylic acids or their pharmaceutical acceptable salts are blended with choline or pharmaceutical acceptable salts of choline such as choline citrate or choline bitartrate. For example, ibuprofen can be blended with choline citrate to give a formulation which does not upset the stomach. Also gemfibrozil can be blended with choline citrate to give a composition having an enhanced anti-lipidemic effect.

4

EXAMPLE 1

The following is a general method for making the choline salts of the present invention: To a round bottom boiling flask fitted with a stirring apparatus and reflux condenser is added 0.1 mole of the sodium salt of the non-steriodal carboxylic acid or anti-lipidemic carboxylic acid dissolved in 500 mls of isopropyl alcohol. Then, 0.1 mole of choline chloride is slowly added. When all the choline chloride is added, the solution is then refluxed for an hour and cooled to 25° C. The sodium chloride which forms is filtered and the solvent evaporated under reduced pressure. The resulting choline salts are then dried under vacuum or subjected to crystallization.

EXAMPLE 2

Following the procedure of Example 1, ibuprofen (0.1 mole) is reacted with choline chloride (0.1 mole) to give choline ibuprofenate.

EXAMPLE 3

Following the procedure of Example 1, gemfibrozil (0.1 mole) choline chloride (0.1 mole) to give choline gemfibrozilate.

EXAMPLE 4

Following the procedure of Example 1, naproxen (0.1 mole) is reacted with choline chloride (0.1 mole) to give choline naproxenate.

EXAMPLE 5

Following the procedure of Example 1, clofibric acid (0.1 mole) is reacted with choline chloride (0.1 mole) to give choline clofibrate.

EXAMPLE 6

200 mg of ibuprofen are mixed with 200 mg of choline dihydrogen tartrate. The active ingredients are triturated and q.s. with lactose to selected capsule size.

EXAMPLE 7

500 mg of gemfibrozil are mixed with 200 mg of choline dihydrogen citrate. The active ingredients are triturated and q.s. with lactose to selected capsule size.

It is to be understood that the forms of the invention herein are to be taken as preferred examples of the same, and that various changes may be made without departing from the spirit of the invention or scope of the subjoined claims.

What is claimed is:

1. A compound of the formula:

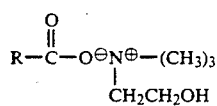

wherein

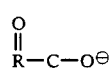

is a non-steroidal anti-inflammatory carboxylic acid selected from the group comprising the arylacetic acids, the arylpropionic acids, the fenamic acids, the biphenyl carboxylic acids and the diphenylether carboxylic acids.

2. A compound of the formula

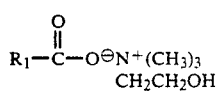

wherein

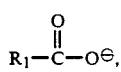

is a carboxylic acid having anti-hyper lipoproteinenic activity selected from the group comprising clofibric acid, gemfibrozil, 5, 8, 11, 14, 17 - eicosapentaenoic acid, oxiniacic acid, and nicotinic acid.

3. A pharmaceutical composition having less stomach irritation comprising: choline or its acceptable pharmaceutical salt; a non steroidal anti-inflammatory carboxylic acid selected from the group comprising the arylacetic acids, the aryl propionic acids, the fenamic acids, the biphenylcarbodylic acids and a pharmaceutical inert carrier.

4. The compound of claim 1 where the carboxylic acid is an aryl acetic acid.

5. The compound of claim 1 where the carboxylic acid is an aryl propionic acid.

6. The compound of claim 5 wherein the carboxylic acid is ibuprofen.

7. The compound of claim 5 wherein the carboxylic acid is naproxen.

8. The compound of claim 5 wherein the carboxylic acid is ketoprofen.

9. A pharmaceutical composition suitable for reducing cholesterol levels comprising: choline or its acceptable pharmaceutical salt; an anti-hyperlipidemic carboxylic acid selected from the group of clofibric acid, gemfibrozil, clinofibrate, bezafibrate ciprofibrate, xenbucin, acipimox, acifran, 5, 8, 11, 14, 17 eicosapentaenoicacid, oxiniacic acid and nicotinic acid and a pharmacetical acceptable carrier.

10. The composition of claim 9 wherein the carboxylic acid is clofibric acid.

11. The compositions of claim 9 wherein the carboxylic acid is gemfibrozil.

12. The composition of claim 9 wherein the carboxylic acid is clinofibrate.

13. The composition of claim 9 wherein the carboxylic acid is bezafibrate.

14. The compositions of claim 9 wherein the carboxylic acid is ciprofibrate.

15. The composition of claim 9 wherein the carboxylic acid is xenbucin.

16. The composition of claim 9 wherein the carboxylic acid is acipimox.

17. The composition of claim 9 wherein the carboxylic acid is acifram.

18. The composition of claim 9 wherein the carboxylic acid is 5, 8, 11, 14, 17, Eicosapentaenoic acid.

19. The composition of claim 9 wherein the carboxylic acid is oxiniacic acid.

20. The composition of claim 9 wherein the carboxylic acid is nicotinic acid.

* * * * *